United States Patent [19]

White

[11] Patent Number: 4,861,733
[45] Date of Patent: Aug. 29, 1989

[54] CALCIUM PHOSPHATE BONE SUBSTITUTE MATERIALS
[75] Inventor: Eugene W. White, Rossiter, Pa.
[73] Assignee: Interpore International, Irvine, Calif.
[21] Appl. No.: 14,466
[22] Filed: Feb. 13, 1987
[51] Int. Cl.$^4$ .......... A61F 1/24; C01B 25/32; C04B 35/00
[52] U.S. Cl. .......... 501/1; 423/305; 433/201.1; 623/16
[58] Field of Search .......... 433/201.1; 623/16; 501/1; 423/305

[56] References Cited
U.S. PATENT DOCUMENTS

| | | | |
|---|---|---|---|
| 3,787,900 | 1/1974 | McGee | 433/201.1 |
| 3,929,971 | 12/1975 | Roy | 623/16 |
| 4,113,500 | 9/1978 | Ebihara et al. | 623/16 |
| 4,230,455 | 10/1980 | Hidaka et al. | 433/202.1 |
| 4,376,168 | 3/1983 | Takani et al. | 501/1 |
| 4,654,314 | 3/1987 | Takagi et al. | 501/1 |
| 4,693,986 | 9/1987 | Vit et al. | 501/1 |
| 4,737,411 | 4/1988 | Graves et al. | 433/201.1 |

FOREIGN PATENT DOCUMENTS

| | | | |
|---|---|---|---|
| 3123460 | 2/1982 | Fed. Rep. of Germany | 623/16 |
| 3445731 | 6/1986 | Fed. Rep. of Germany | 623/16 |
| 12649 | 1/1983 | Japan | 623/16 |

Primary Examiner—John Doll
Assistant Examiner—Wayne A. Langel
Attorney, Agent, or Firm—Cooper & Dunham

[57] ABSTRACT

Calcium phosphates useful as bone substitute material or for the manufacture of prosthetic devices have been prepared from calcium hydroxyapatite material which has a uniformly permeable microporous structure characterized by a substantially uniform pore volume in the range from about 10 to about 90% and by a pronounced three-dimensional fenestrate structure corresponding to the microstructure of the porous carbonate echinoderm or scleractinian coral skeletal material of marine life by reacting said calcium hydroxyapatite material which has a calcium to phosphorus atomic ratio of about 1.66 with a phosphate-contributing or phosphorus-contributing moiety or with a calcium-contributing or calcium oxide-contributing moiety so as to alter the calcium to phosphorus Ca/P atomic ratio to yield a calcium phosphate material retaining the above-described microstructure of the porous carbonate echinoderm or scleractinian coral skeletal material but having a calcium to phosphorus Ca/P atomic ratio less than or greater than 1.6, such as a calcium phosphate material comprising dicalcium phosphate and/or tricalcium phosphate and having a calcium to phosphorus Ca/P atomic ratio in the range 1.0–1.5 when the calcium hydroxyapatite material is reacted with said phosphate-contributing or phosphorus-contributing moiety or a calcium phosphate material having a calcium to phosphorus Ca/P atomic ratio greater than 1.66 up to 2.0 when the calcium hydroxyapatite material is reacted with said calcium-contributing or calcium oxide-contributing moiety and comprising tetracalcium phosphate.

44 Claims, 1 Drawing Sheet

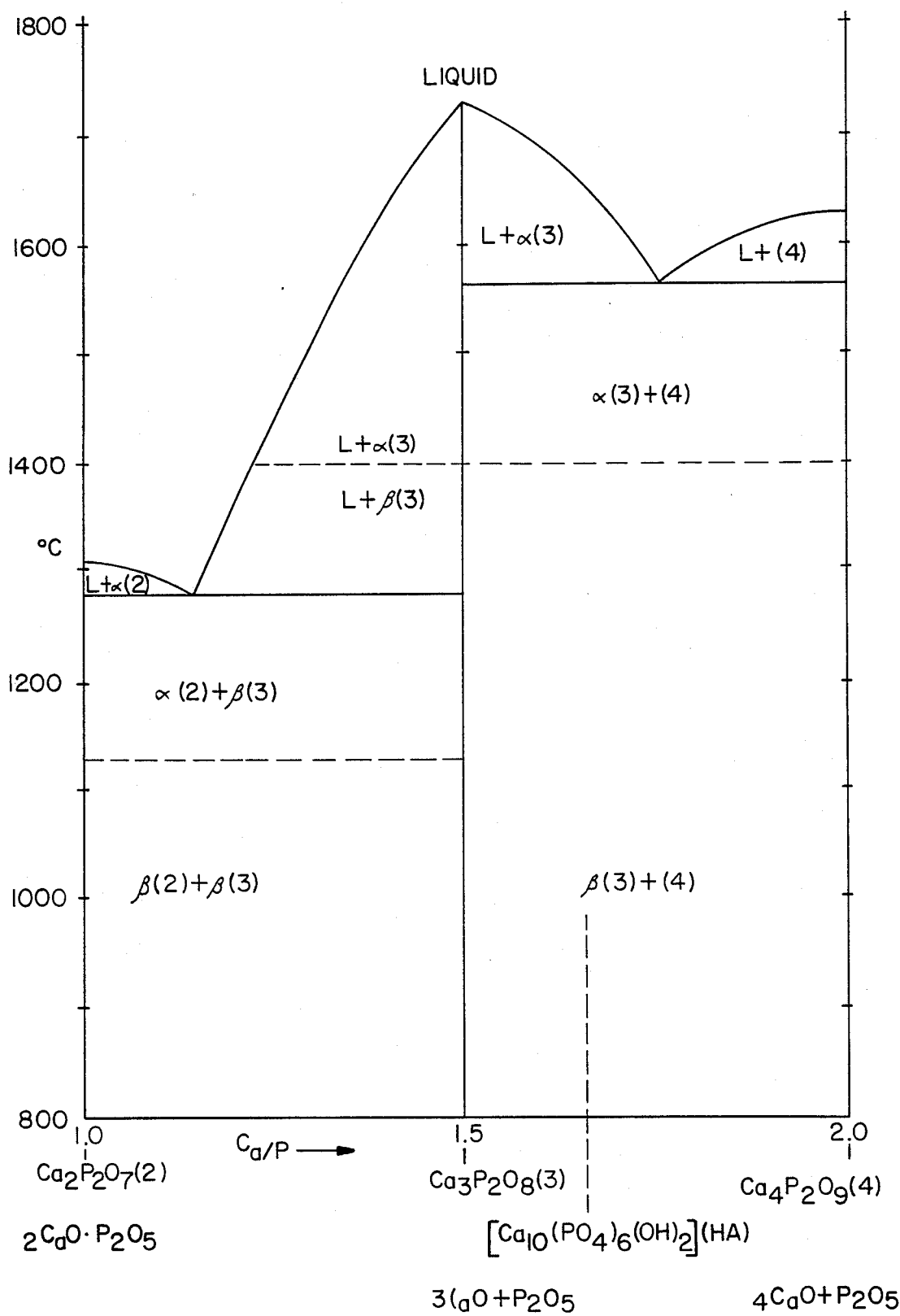

CALCIUM PHOSPHATE BONE SUBSTITUTE MATERIALS

BACKGROUND OF THE INVENTION

Porous carbonate echinoderm or scleractinian skeletal material of marine life has a unique structure. This material has a uniformly permeable microporous structure characterized by a substantially uniform pore volume in the range from about 10 to about 90% and by a pronounced three-dimensional fenestrate structure. The microstructure of this material is somewhat similar to the cancellous structure characteristic of boney tissue or bone. Because of this unique microstructure of the porous carbonate echinoderm or scleractinian coral skeletal material of marine life these materials would appear to be useful as bone substitute material. However, the carbonate of this material, such as provided in echinoid spine calcite and Porites skeletal aragonite, do not have the desired durability for employment as bone substitutes. These materials, however, including their unique above-mentioned microporous structure, have been replicated in other materials, such as metals, which would appear to possess better physical properties from the point of strength and durability while at the same time providing the distinct unique microporous structure of the original porous carbonate coral skeletal material U.S. Pat. No. 3,890,107 discloses techniques, and products resulting therefrom, for replicating the unique microporous structure of the above-mentioned coral material including derivatives thereof.

It is also known that the aforementioned coral materials may be converted by chemical techniques employing a hydrothermal exchange reaction so as to convert the carbonate or the calcium carbonate of the coral material to hydroxyapatite while at the same time retaining the unique microstructure of the coral material. U.S. Pat. No. 3,929,971 discloses a hydrothermal exchange reaction for converting the porous carbonate skeletal material of marine life into a phosphate or hydroxyapatite skeletal material possessing the same microstructure as the carbonate skeletal material. These synthetic hydroxyapatite materials have been produced commercially and are available from Interpore International Inc., Irvine, Calif., under the tradename Interpore-200, which is derived from certain coral of the genus Porites which have an average pore diameter of about 200 μm and under the tradename Interpore-500 derived from certain members of the family Goniopora,, which have pore diameters of about 500 μm.

These special Interpore hydroxyapatite materials have also been identified as replamineform hydroxyapaptite and coralline hydroxyapatite. Interpore-200 and Interpore-500 have been found to be useful as bone substitute materials. More information concerning these materials is to be found in the article by Eugene White and Edwin C. Shors entitled "Biomaterial Aspects of Interpore-200 Porous Hydroxyapatite", which appeared in *Dental clinics of North America*, Vol. 30, No. 1, January 1986, pp. 49–67.

In addition to the above-described materials which have the unique microstructure of porous skeletal coral material, other materials have been proposed as bone substitute materials, see U.S. Pat. Nos. 4,097,935, 4,195,366, 4,308,064 and 4,314,380. For the most part, however, these other bone substitute materials which do not possess the unique structure of coral material which is possessed by Interpore-200 and Interpore-500, have not been completely satisfactory.

Despite the fact that calcium phosphates have been well investigated, see the publication entitled *Bioceramics of Calcium Phosphate*, particularly Chapter 1 of F. C. M. Driessens entitled "Formation and Stability of Calcium Phosphates in Relation to the Phase Composition of the Mineral in Calcified Tissues", and Chapter 5 by Klaas deGroot entitled "Ceramics of Calcium Phosphates: Preparation and Properties", other calcium phosphate materials which possess the advantages and the unique coral-derived microporous structure of Interpore-200 and Interpore-500 have not yet been satisfactorily produced.

The disclosures of the above-identified patents and publications are herein incorporated and made part of this disclosure.

The physical properties of the apatite bone substitute materials which possess the unique microstructure of skeletal material, such as Interpore-200 and Interpore-500, although satisfactory, do not provide for all the needs of surgeons employing the same as bone replacements and bone implant materials. For example, some surgeons would prefer a similar material but made up of a more readily absorbable or resorbable material, such as a material which would be absorbed by the body or would disintegrate within about six months to two years. Other surgeons would prefer to employ a similar such material which is more refractory, lasts about ten years, more or less, or be substantially permanent. The presently available materials, such as Interpore-200 and Interpore-500, possess properties somewhat intermediate and are rather fixed since these materials are comprised substantially only of hydroxyapatite.

It is an object of this invention to provide bone substitute materials and a method for their manufacture derived from hydroxyapatite or other calcium phosphate bone substitute material having the unique microstructure of the porous carbonate echinoderm scleractinian coral skeletal material of marine life.

It is another object of this invention to provide bone substitute materials derived from hydroxyapatite material or other calcium phosphate bone substitute material which has the unique microstructure of the porous carbonate echinoderm or scleractinian coral skeletal material of marine life or the cancellous structure characteristic of boney tissue or bone but which is chemically different from hydroxapatite or the material from which it is derived but yet possessing substantially the same microstructure of the material from which it is derived and which is relatively more or less readily absorbable by the body.

How these and other objects of the invention are achieved will become apparent in the light of the accompanying disclosure made with reference to the accompanying drawing which illustrates a portion of the phase diagram of the system $CaO-P_2O_5$.

SUMMARY OF THE INVENTION

Calcium phosphates chemically differing from hydroxapatite and useful as bone substitute materials for the manufacture of prosthetic devices have been prepared from hydroxyapatite material. The hydroxyapatite material employed in one embodiment of this invention for the manufacture of these calcium phosphates is desirably itself useful as a bone substitute material and has the cancellous structure characteristic of boney tissue or bone or a uniformly permeable microporous structure characterized by a substantially uniform pore volume in the range from about 10–90% and by a pronounced three-dimensional fenestrate material corresponding to the microstructure of the porous carbonate echinoderm scleractinian coral skeletal material of marine life.

The calcium phosphates of this invention in accordance with one embodiment are prepared by reacting hydroxyapatite $Ca_{10}(PO_4)_6(OH)_2$ material which has the above-described microporous structure and which has a calcium to phosphorus atomic to phosphorus atomic ratio of about 1.66 with one or more other materials, calcium or phosphorus compounds, so as to produce a reaction product wherein the Ca/P ratio is less than 1.66 or greater than 1.66.

Suitable such hydroxyapatite material is the above-described Interpore-200 and Interpore-500. The hydroxy-apatite material is reacted with a phosphate-contributing or phosphorus-contributing moiety or with a calcium-contributing or calcium oxide-contributing moiety so as to alter the calcium to phosphorus Ca/P atomic ratio of the resulting reaction product to yield a calcium phosphate material which, while retaining the above-described microstructure of the porous carbonate echinoderm or scleractinian coral skeletal material, has an altered, increased or decreased, calcium to phosphours Ca/P atomic ratio greater than 1.6 or less than about 1.6. The resulting calcium phosphate has a Ca/P atomic ratio in the range 1. .5, or less than 1.66 when hydroxyapatite material is reacted with a phosphate-contributing or phosphorus-contributing moiety. This resulting calcium phosphate material would contain tricalcium phosphate or dicalcium phosphate or mixtures thereof, depending upon the extent of the addition and the reaction of the phosphate-containing or phosphorus-contributing moiety with the hydroxyapatite material being treated. By employing, instead of phosphate-contributing or phosphorus-contributing moiety for reaction with the hydroxyapatite material, a calcium-contributing or calcium oxide-contributing moiety for reaction with the hydroxyapatite material, there would be produced a calcium phosphate material which would have a Ca/P atomic ratio greater than 1.66 up to about 2.0 and which would comprise tetracalcium phosphate $Ca_4P_2O_9$, usually a mixture of tetracalcium phosphate and hydroxyapatite.

The calcium phosphates produced in accordance with this invention, e.g. from hydroxyapatite material, are produced by adding to or incorporating in the hydroxyapatite material the phosphate-contributing or phosphorus-contributing moiety in the instance when it is desired to produce a calcium phosphate material having a lower Ca/P atomic ratio in the range 1.0–1.5, such as a calcium phosphate material containing dicalcium phosphate and tricalcium phosphate, or by adding to or incorporating in the hydroxyapatite material a calcium-contributing or calcium oxide-contributing moiety when it is desired to produce a calcium phosphate material having Ca/P atomic ratio above 1.6, such as greater than 1.66 up to 2.0, and to produce a calcium phosphate material which contains therein tetracalcium phosphate.

The above-mentioned moieties for reaction with the calcium phosphate or hydroxyapatite material whose Ca/P ratio is to be altered, are added to or incorporated therein, preferably in the form of an aqueous solution or finely divided suspension, by employing water-soluble moieties or by employing very finely divided moieties in suspension in a suitable carrier, such as an aqueous suspension. These moieties are added to the hydroxyapatite material so as to substantially completely and uniformly occupy and coat or cover the surfaces, internal and external, of the hydroxyapatite or calcium phosphate material undergoing treatment. By alternately and successively wetting and drying the material to be treated, a substantial layer or amount of the desired moiety can be deposited onto and within the material.

Thereupon, the treated calcium phosphate material, such as hydroxyapatite, is heated or fired to an elevated temperature without melting to carry out the solid state reaction to effect the alteration of the Ca/P atomic ratio, such as from a value of about 1.6 characteristic of hydroxyapatite up to 2.0 characteristic of tetracalcium phosphate or to a lower value of 1.0 characteristic of dicalcium phosphate. A firing temperature up to about 1350°–1550° C. is employed for the production of a calcium phosphate product containing tetracaclium phosphate or a firing temperature up to about 1275° C., such as a temperature in the range 1000°–1250° C. for a dicalcium phosphate and/or a tricalcium phosphate product. At these relatively firing lower temperatures there would be produced upon the employment of phosphate-contributing or phosphorus-contributing moiety, a resulting treated calcium phosphate which, as indicated, would have a Ca/P atomic ratio less than 1.6, such as a ratio of less than 1.5 or in the range 1.0–1.5, and containing dicalcium phosphate or tricalcium phosphate or mixtures thereof.

Suitable phosphate-contributing or phosphorus-contributing moieties for use in the practice of this invention include phosphoric acid, $H_3PO_4$ the ammonium phosphates, such as diammonium phosphate $(NH_4)_2HPO_4$ and other, preferably water-soluble and volatilizable phosphate compounds. Suitable calcium oxide-contributing or calcium-contributing moieties useful in the practice of this invention include the water-soluble, also preferably volatilizable calcium compounds. Particularly useful are solutions and/or finely divided suspensions of calcium oxide, calcium hydroxide, calcium nitrate and other calcium organic compounds, such as calcium acetate, calcium butyrate and calcium propionate.

The firing operation during which the calcium phosphate material, e.g. hydroxyapatite, undergoing alteration of its Ca/P ratio to a higher or lower value along with the added calcium-contributing or phosphorus-contributing moiety is carried out in an inert or, preferably, in an oxidizing atomsphere, e.g. in the presence of air or oxygen, for a sufficient period of time to effect the desired alteration of the Ca/P ratio of the calcium phosphate being fired to a higher or lower value. The lowest Ca/P ratio sought or desired is 1.0, equivalent to dicalcium phosphate, and the highest Ca/P ratio sought or desired is 2, equivalent to tetracalcium phosphate.

The duration of firing varies with the firing temperature employed, a higher firing temperature tending to increase the reaction rate with the result that shorter firing times are experienced. For example, for the production of a fired calcium phospphate material having a Ca/P ratio of 2.0, the firing and temeprature is desirably carried out at a temperature in the range 1300°–1550° C. The firing time is longer, about 12–24 hours, more or less, when carried out at a firing temperature of about 1300° C. and shorter, about 6–16 hours, more or less, when the firing temperature employed is about 1300°–1550° C. When it is desired to produce a fired calcium phosphate material having a lower Ca/P ratio down to 1.0, the firing temperature employed is desirably in the range from about 1000 to about 1250° C., preferably in the range 1000°-1125° C. A lower firing temperature would require a longer firing time, in the range about 8-20 hours and a higher firing temperature would yield a shorter firing time in the range 1-3 hours, more or less. If desired, multiple firing operations, also including multiple additions of a calcium-contributing moiety or a phosphorus-contributing moiety, may be employed.

The firing time required to produce the fired calcium phosphate product of desired quality, composition and Ca/P ratio, also depends upon the calcium-contributing or phosphorus-contributing moiety employed. Some such moieties are more effective reactive than others at a given firing temperature. The use of a firing adjuvant to improve or increase the effectiveness or reactivity of the added calcium-contributing or phosphorus-contributing moiety to the calcium phosphate material undergoing firing is helpful, particularly in reducing the firing time required. The use of a scavenger when the calcium-contributing moiety or the phosphorus-contributing moiety includes one or more elements which would be undesirable to be present in the finished fired calcium phosphate product, might also tend not only to decrease the firing time, but also increase the effectiveness of the calcium contributing or phosphorus-contributing moiety employed in the firing operation. In general, the firing operation is carried out for a sufficient period of time so that the finished fired calcium phosphate product has the desired Ca/P ratio with respect to the starting calcium phosphate material.

BRIEF DESCRIPTION OF THE DRAWING

The sole FIGURE of the Drawing is a binary phase diagram of the system $CaO-P_2O_5$, the phase boundaries for the phases of interest, $Ca_2P_2O_7$, $Ca_2P_2O_8$ and $Ca_4P_2O_9$, being represented as sharp lines.

BRIEF DESCRIPTION OF THE INVENTION

Tests were carried out to alter hydroxyapatite material having the above-described microstructure of porous carbonate echinoderm or scleractinian coral skeletal material of marine life, said hydroxyapatite material having a Ca/P atomic ratio of 1.66 to a lower Ca/P ratio. Specifically, experiments were carried out to convert the hydroxyapatite material to tricalcium phosphate, more specifically, whitlockite beta-$Ca_3P_2O_8$ This work was carried out to produce from the hydroxyapatite material, tricalcium phosphate which is more resorbable than hydroxyapatite while at the same time retaining the microstructure of the starting hydroxyapatite material.

In these tests blocks of hydroxyapatite material Interpore 500 or IP 500 measuring $15 \times 30 \times 30$ mm were suspended from a stainless steel wire loop and lowered into a concentrate 1:2 aqueous solution of $(NH_4)_2HPO_4:H_2O$. After a two minute soaking in the solution, the blocks were removed and the treating solution removed by shaking the blocks. The blocks were placed on an alumina substrate and rotated in 90° increments every few minutes. After air drying for about 2 hours, the blocks on the alumina substrate were placed in a warm (50° C.) oven. The rotation was again continued every few minutes for an hour and the temperature increased to 80° C. and the blocks left in the oven overnight. The dry weight of the blocks increased by about 12.6%. Thereupon, the blocks were heated in an oven over a period of 2 ¾ hours to about 1170° C. and maintained at about this temperature (heat soaked) for about 2 hours. Thereupon the blocks were reduced in temperature to about 100° C. or lower over a period of 8 hours. It was observed that the final fired or heated weight of the blocks increased about 4.1% above the starting hydroxyapatite material.

Upon examination, the fired hydroxyapatite blocks were found to have been converted to 60% whitlockite or beta-$Ca_3P_2O_8$ and 40% alpha-$Ca_2P_2O_7$. Whitlockite, the familiar form of tricalcium phosphate, is absorbed in the body more readily than hydroxyapaptite and the tricalcium phosphate alpha-$Ca_2P_2O_7$, in turn, is more quickly absorbable than whitlockite. From the various tests carried out following the above procedures and employing different hydroxyapatite starting material, the following results were obtained.

TABLE NO. 1

| | | SUMMARY OF CONVERSION RUN DATA | | | |
|---|---|---|---|---|---|
| Starting Hydroxyapatite | Run # | Added (dry) w % Phosphate $(NH_4)_2HPO_4$ | % $Ca_3P_2O_8$ (Whitlockite) | % $\alpha$-$Ca_2P_2O_7$ | % Hydroxyapatite |
| IP500 | HT-22 | 12.6% | 60 | 40 | — |
| IP500 | HT-21A | 21% | 60 | 40 | — |
| IP500 | HT-21B | 11.9 | 70 | 30 | — |
| IP500 | HT-21C | 36 | 70 | 30 | — |
| IP200 | HT-21D | 15 | 85 | 15 | — |
| Bone HA | HT-20-BH-15 | 29% | 85 | 15 | — |
| Bone HA | HT-19-BH-13 | NA* | 90 | 10 | — |
| IP500 | HT-18A | 32.8 | 60 | 40 | — |
| | HT-18B | 32.8 | 60 | 40 | — |
| IP500 | HT-23A | 4.2% | 70 | 15 | 15 |
| IP500 | HT-23B | 0.8% | 70 | — | 20 |
| IP200 | HT-23C | 3.0 | 60 | — | 40 |
| IP500 | HT-24A | NA? | 60 | — | 40 |
| IP200 | HT-24B | NA? | 80 | — | 20 |
| IP500 | HT-24C | NA? | 80 | 10** | 10 |
| IP200 | HT-24D | NA? | 90 | 10** | — |
| IP500 | HT-24E | 8.3 | 80 | 10** | 10 |
| IP200 | HT-24F | 5.1 | 90 | — | 10 |

*NA - Not Available
**Mixture of $\alpha$ and $\beta$-$Ca_2P_2O_7$

Referring now to the drawing which is a binary phase diagram of the system CaO-P$_2$O$_5$, the phase boundaries for the phases of interest, Ca$_2$P$_2$O$_7$, Ca$_2$P$_2$O$_8$ and Ca$_4$P$_2$O$_9$, are represented as sharp lines. In the interpretation of this binary diagram, if the Ca/P ratio is not almost exactly 1.5, then traces of either Ca$_2$P$_2$O$_7$ will appear or traces of hydroxyapatite will remain, depending upon which side of the Ca$_3$P$_2$O$_8$ boundary the bulk composition occurs. It should be understood, therefore, that pure tricalcium phosphate crystalline would be difficult to obtain and the usual result is that a less pure product is obtained ±5-10%. It is pointed out that hydroxyapatite which has a nominal Ca/P ratio of 1.6 does not actually plot on the diagram because it contains some hydroxyl groups. It was observed that the hydroxyapatite material tested, the IP 200 and the IP 500, maintained its hydroxyapatite crystal structure even when heated for 2 hours at 1350° C. Thus, the resulting fired products Ca$_3$P$_2$O$_8$ and Ca$_2$P$_2$O$_7$ derived from the resulting ammonium phosphate treated hydroxyapatite were not just the result of heat treatment.

Tests were also carried out involving the heat treatment of hydroxyapatite material, such as Interpore200, at a temperature of 1500° C. and these tests did not show any significant conversion of hydroxyapatite to whitlockite.

Additional tests were carried out involving the treatment of hydroxyapatite material, such as Interpore-200, with a phosphorus-contributing or phosphate-contributing moiety, such as phosphoric acid, and an ammonium phosphate, such as diammonium phosphate (NH$_4$)$_2$HPO$_4$ In these tests the hydroxyapaptite materials were also immersed in or soaked in solutions of phosphoric acid H$_3$PO$_4$ or (NH$_4$)$_2$HPO$_4$, dried and then fired in air at a temperature of 1175° C. for about 2 hours. It was observed that dipping or immersing the hydroxyapaptite material in concentrated phosphoric acid H$_3$PO$_4$, followed by drying and firing at 1175° C. resulted in substantially complete conversion of the hydroxyapatite to produce a material containing about 15-20% whitlockite and a major amount of the remainder comprising dicalcium phosphate, particularly beta-Ca$_2$P$_2$O$_7$. It was observed that one sample of hydroxyapatite so treated contained a small amount of delta-Ca(PO$_4$)$_2$. This material delta-Ca(PO$_4$)$_2$ would be unstable in contact with water or body fluids.

In the above tests, when the hydroxyapatite material was immersed in 1:1 H$_3$PO$_4$/H$_2$O solution followed by drying and firing at 1175° C., the hydroxyapatite was completely converted to 5 0% whitlockite and 30-50 alpha-Ca$_2$P$_2$O$_7$. In with those hydroxyapatite materials which had been treated to produce beta-Ca$_2$P$_2$O$_7$, the alpha-Ca$_2$P$_2$O$_7$ materials were considerably stronger than the starting hydroxyapatite material. When hydroxyapatite material was immersed in a 1:3 H$_3$PO$_4$/H$_2$O solution and dried and at 1175° C., there was produced a fired material comprising 70% hydroxyapatite and 30% whitlockite.

In the treatment of hydroxyapatite with diammonium phosphate solutions, one sample of hydroxyapatite was immersed in a hot saturated solution of diammonium phosphate, dried and fired at 1150° C. for 2.5 hours. The resulting fired sample was predominantly, about 70%, whitlockite with minor amounts of hydroxyapatite, about 10%, and alpha-Ca$_2$P$_2$O$_7$, about 20%. Another sample of hydroxyapatite material, when immersed in a 1:3.75 solution of (NH$_4$)$_2$HPO$_4$:H$_2$O solution, and dried and fired at 1175° C. for 2 hours yielded a material comprising 30% hydroxyapatite, 70% whitlockite and a trace of alpha-Ca$_2$P$_2$O$_7$.

Another sample, 10×15×82 mm of hydroxyapatite, was dipped into a 1:3 (NH$_4$)$_2$HPO$_4$:H$_2$O solution for 10 minutes and dried while suspending in air. When this material was fired for 2.25 hours at 1175° C., the top end of the fired material was converted to 10% hydroxyapatite, 80% whitlockite and 10% alpha-Ca$_2$P$_2$O$_7$. The bottom end of this vertically hung piece, however, presumably having a high concentration of phosphate therein, was converted to 80% whitlockite and 20% alpha Another similarly treated hydroxyapatite Ca$_2$P$_2$O$_7$ and produced a sample was fired for 2 hours at 1175° C. finished material comprising 30% hydroxyapatite and 70% whitlockite with traces of alpha-Ca$_2$P$_2$O$_7$. The results of these tests are set forth in accompanying Table No. 2.

TABLE NO. 2

| SAMPLE TREATMENT | | Sample code | Time at Temp (Hrs) | Temp °C. | % H.A. | % White lockite | % α-Ca$_2$P$_2$O$_7$ | % β Ca$_2$(PO$_2$)$_2$ | % α-Ca(PO$_4$)$_2$ | % Aragonite | % Calcite |
|---|---|---|---|---|---|---|---|---|---|---|---|
| H$_3$PO$_4$ Soak | | x | 2.5 | 1175 | — | 15 | — | 70 | 15 | — | — |
| 1:1 H$_3$PO$_4$/H$_2$O Dip | | y | 2.5 | 1175 | — | 60 | 40 | — | — | — | — |
| 1:1 H$_3$PO$_4$/H$_2$O Dip & Rinse | | z | 2.5 | 1175 | — | 50 | 50 | — | — | — | — |
| 2:1 (NH$_4$)$_2$H(PO$_4$)/Coral | | AT-01 | 72 | 217 | 100 | — | — | — | — | — | — |
| 1:1 (NH$_4$)$_2$ + (PO$_4$)/Coral + 1% Mg. | | AT-02 | 72 | 217 | 90 | 10 | — | — | — | — | — |
| 1:1 (NH$_4$) SOLN/Coral + 1% Mg. | | AT-04 | 72 | 217 | 90 | 10 | — | — | — | — | — |
| 0.5:1 SOLN/Coral + 1% Mg. | | AT-05 | 72 | 217 | 50 | 10 | — | — | — | 20 | 20 |
| 1:3 (NH$_4$)H(PO$_4$):H$_2$O | | HT-10B | 2.5 | 1175 | — | 80 | 20 | — | — | — | — |
| 2 min. Dip & Dry | | HT-10T | | | 10 | 80 | 10 | — | — | — | — |
| 1:3 H$_3$PO$_4$/H$_2$O | 15 min. | HT-11 | | | | 70 | 30 | — | — | — | — |
| H$_3$PO$_4$ | 7 min. | HT-12 | | | — | 20 | — | 80 | — | — | — |
| 1:1 H$_3$PO$_4$/H$_2$O | 10 min. | HT-13 | 2.0 | 1175 | — | 60 | 40 | — | — | — | — |
| 1:3 H$_3$PO$_4$/H$_2$O | 5 min. | HT-14 | | | | 70 | 30 | — | — | — | — |
| 1:1 H$_3$PO$_4$/H$_2$O | 6 min. | HT-15 | | | — | 70 | 30 | — | — | — | — |
| 1:3.75 (NH$_4$)$_2$H(PO$_4$)/H$_2$O Dip | | HT-16 | | | 30 | 70 | 5? | — | — | — | — |
| HA #144 Hot Sat. (NH$_4$)$_2$HPO$_4$ | | HT-17 | 2.5 | 1150 | 10 | 70 | 20 | — | — | — | — |

The above-described tests which involved the addition of a phosphate-contributing or phosphorus-contributing moiety, such as phosphoric acid H$_3$PO$_4$ or an ammonium phosphate, such as (NH$_4$)$_2$HPO$_4$, to hydroxyapatite material, such as Interpore-500 and Interpore-200, followed by subsequent heat treatment or firing in the presence of air at an elevated temperature of about 1125°-1175° C. for a number of hours, such as 1.5-2 hours, produced a material which contained tricalcium phosphate. In these tests, as indicated hereinabove, when larger amounts of the phosphate-contributing or phosphorus-contributing moiety were incorporated in the hydroxyapatite undergoing treatment there were produced materials which contained tricalcium phosphate and dicalcium phosphate. In these tests, however, where the hydroxyapatite materials were immersed in a solution of phosphoric acid or diammonium phosphate and then drained, dried and fired, it was not always possible to obtain reproducible results. Further, it has been noted that when the firing of the phosphate-treated hydroxyapatite material was carried out at 1175° C. for conversion of the hydroxyapatite to dicalcium phosphate $Ca_2P_2O_7$, the produced dicalcium phosphate was in both the alpha and beta crystal form or structure. As indicated in the accompanying $CaO$-$P_2O_5$ phase diagram, beta-$Ca_2P_2O_7$ is the low temperature form of dicalcium phosphate.

In order to improve reproducibility of the test results, the phosphate-contributing or phosphorus-contributing moiety, i.e. the aqueous solution of $H_3PO_4$ or ammonium phosphate, e.g. 1:2 $(NH_4)_2HPO_4:H_2O$ was pipetted directly onto the hydroxyapatite material, a block of Interpore-500. This technique eliminated the uncertainty introduced by dipping and soaking and draining the hydroxyapatite material into the treating solution. When pipette additions of the treating solution are made to the hydroxyapatite material, the solution does not immediately completely wet the entire structure. A few minutes are required for the treating solution to wick into all areas or surfaces of the block. This so-called pipette/wick method of addition of the treating solution to the hydroxyapatite material was found to be satisfactory and yielded more or less reproducible results. The results of these tests employing the pipette/wick technique are set forth in accompanying Table No. 3.

and weighed in the range 10.1–16.05 grams. The phase compositions reported in Table No. 3 were obtained by x-ray powder diffraction analysis In the samples designated HT-25, HT-26 and HT-27 reported in Table No. 3 the blocks were handled by dipping and soaking. The pipette/wick method employed for the test series Ht-28 and HT-29 controlled phosphate addition at a predetermined level. It should be noted, as reported in Table No. 3, that the fired weights of the hydroxyapatite blocks were only slightly greater than the starting hydroxyapatite material. This was due not only to loss of $NH_4$ but also to the loss during firing of some structural hydroxyl OH and carbon dioxide $CO_2$.

From the data presented in Table No. 3, it should be noted that ammonium phosphate additions, as small as 2.5% by weight, resulted in approximately 50% tricalcium phosphate yields. A 10% ammonium phosphate addition gave 85–95% conversion. Even the addition of 18% ammonium p did not eliminate some residual hydroxyapatite. Based on the results reported, it would appear that conversion of hydroxyapatite to tricalcium phosphate is preferably carried out by the so-called pipette/wick technique for the addition of 12% $(NH_4)_2HPO_4$ aqueous solution (1:2 aqueous solution) with firing at 1125° C. for 2 hours. Further, satisfactory results would also likely be obtained by employing more concentrated ammonium phosphate solutions and to carry out the draining and drying operations under a reduced atmospheric pressure and at a low temperature, below room temperature.

Additional tests were carried out on hydroxyapatite material, Interpore-500 and Interpore-200, for the conversion of the hydroxyapatite therein to tricalcium phosphate. These tests were carried out using the pipette/wick technique of phosphate addition. The results of these tests are set forth in accompanying Table No. 4.

TABLE NO. 3

BASIC WEIGHT DATA FOR TCP RUNS FIRED AT 1125° C.

| Sample Designation | IP500 Weight | IP500+ Solution | % Phosphate Addition | Fired Weight | % HA | % TCP | Addition Method |
|---|---|---|---|---|---|---|---|
| HT-25-I | 11.75 | 13.3 | 4.4 | 12.2 | 60 | 40 | ↑ |
| -II | 14.1 | 15.2 | 2.6 | 13.9 | 55 | 45 | ↑ |
| -III | 10.1 | 11.1 | 3.3 | 10.1 | 50 | 50 | ↑ |
| -IV | 12.85 | 14.4 | 4.0 | 12.8 | 40 | 60 | ↑ |
| HT-26-I | 10.3 | 15.9 | 18.1 | 10.9 | 15 | 85 | Dip/Soak |
| -II | 10.6 | 16.7 | 19.2 | 11.3 | 10 | 90 | |
| -III | 13.2 | 18.9 | 14.4 | 13.8 | 5 | 95 | |
| -IV | 10.9 | 14.9 | 12.2 | 11.3 | 5 | 95 | |
| HT-27-I | 11.0 | 14.4 | 10.3 | 11.3 | 10 | 90 | ↓ |
| -II | 15.8 | 18.2 | 5.1 | 15.8 | 40 | 60 | ↓ |
| -III | 14.2 | 16.5 | 5.4 | 14.2 | 20 | 80 | ↓ |
| HT-28-I | 10.5 | 11.3 | 2.5 | 10.4 | 60 | 40 | ↑ |
| -II | 12.9 | 14.85 | 5.0 | 13.0 | 30 | 70 | ↑ |
| -III | 12.2 | 14.95 | 7.5 | 12.3 | 20 | 80 | Pipette/ |
| -IV | 11.35 | 14.76 | 10.0 | 11.55 | /7 | 93 | Wick |
| HT-29-I | 13.6 | 15.65 | 5.0 | 13.65 | 30 | 70 | |
| -II | 11.85 | 15.4 | 10.0 | 12.15 | 5 | 95 | ↓ |
| -III | 16.65 | 22.89 | 12.5 | 17.15 | 10 | 90 | ↓ |
| -IV | 12.8 | 18.56 | 15.0 | 13.50 | 5 | 95 | ↓ |

In the reported Table No. 3 tests, the hydroxyapatite blocks, Interpore-500 blocks, measured $30 \times 30 \times 50$ mm

TABLE NO. 4

| Sample # | OVEN DRY WT. | WITH ADDED PHOSPHATE | % SOLN. GAIN | OVEN DRY TREATED | FIRED WT. | % FIRED GAIN | % DRY $(NH_4)_2HPO_4$ PHOSPHATE ADDED | % HA | % WHIT | % $\beta$-$CA_2P_2O_7$ |
|---|---|---|---|---|---|---|---|---|---|---|
| IP 500 Precursor | | | | | | | | | | |
| HT-30A-I | 11.3 | 13.0 | 15 | 11.8 | 11.3 | 0 | 4.4 | 15 | 85 | — |

TABLE NO. 4-continued

| Sample # | OVEN DRY WT. | WITH ADDED PHOSPHATE | % SOLN. GAIN | OVEN DRY TREATED | FIRED WT. | % FIRED GAIN | % DRY (NH$_4$)$_2$HPO$_4$ PHOSPHATE ADDED | % HA | % WHIT | % β-CA$_2$P$_2$O$_7$ |
|---|---|---|---|---|---|---|---|---|---|---|
| HT-30A-II | 15.5 | 20.5 | 30 | 16.9 | 15.7 | 1.3 | 9.0 | 5 | 90 | 5 |
| HT-30A-III | 15.1 | 21.9 | 45 | 17.2 | 15.7 | 4.0 | 13.9 | 2-5 | 85 | 10 |
| HT-30A-IV | 13.9 | 22.2 | 60 | 16.5 | 14.7 | 5.8 | 18.7 | — | 85 | 15 |
| HT-30A-V | 13.6 | 23.8 | 75 | 16.6 | 14.6 | 7.4 | 22.1 | — | 85 | 15 |
| HT-30A-VI | 11.7 | 11.7 | (0.0) | 11.5 | 11.3 | −3.4 | −1.7 | 80 | 20 | — |
| IP 200 Precursor | | | | | | | | | | |
| HT-30B-I | 10.1 | 11.86 | 17.4 | 10.6 | 10.2 | 1.0 | 5.0 | 10 | 90 | Tr? |
| HT-30B-II | 10.0 | 10.75 | 7.5 | 10.0 | 9.9 | −1.0 | 0.0 | 30 | 70 | — |
| HT-30B-III | 9.7 | 12.6 | 30 | 10.4 | 9.9 | 2.1 | 5.2 | 10 | 90 | 2-5 |
| HT-30B-IV | 8.9 | 12.9 | 45 | 10.0 | 9.3 | 4.5 | 12.4 | — | 85 | 15 |
| HT-30B-V | 8.5 | 13.6 | 60 | 10.0 | 9.1 | 7.1 | 17.6 | — | 90 | 10 |
| HT-30B-VI | 9.9 | 12.1 | 22.5 | 10.4 | 9.9 | 0.0 | 5.0 | 10 | 85 | 5 |
| HT-30B-VII | 9.8 | 9.8 | (0.0) | 9.8 | 9.6 | −2.0 | 0.0 | 90 | 10 | — |

In the tests reported in Table No. 4 a 1:2 (NH$_4$)$_2$HPO$_4$:H$_2$O solution was employed and the treated hydroxyapatite samples were fired at 1125° C. for 2.3 hours. As indicated in Table No. 4, the hydroxyapatite sample materials readily converted to tricalcium phosphate. The hydroxyapatite was substantially completely eliminated and dicalcium phosphate appeared in the finished fired samples only as a trace constituent.

In order to determine if firing temperature had an effect on dicalcium phosphate yield for a given phosphate addition, three samples which had been fired at a temperature of 1125° C. were refired at a temperature of 1250° C. Accompanying Table No. 5 summarizes the results of these tests and indicates that the higher firing temperature produces a higher yield of dicalcium phosphate and reduces the concentration of hydroxyapatite.

TABLE NO. 5

Reheat Experiment to See Effect of 1125° C. vs 1250° C. on Yield of TCP/DCP.

| 1250° C. Reheat Designation | % HA | % TCP | % DCP | 1125° C. Reheat Designation |
|---|---|---|---|---|
| HT-31-II | — | 80 | 20 | |
| | 5-10 | 90-95 | — | HT-29 IV |
| HT-31-III | 30 | 65 | — | |
| | 10-20 | 80-90 | — | HT-28 III |
| HT-31-IV | — | 70 | 30 | |
| | — | 85 | 15 | HT-30A V |

In the foregoing tests there was employed the addition of a phosphate-contributing or phosphorus-contributing moiety to the hydroxyapatite material so as to alter the Ca/P ratio thereof from 1.66 to a lower value approaching 1.0, the value for dicalcium phosphate or to a lower value of 1.5, the value for tricalcium phosphate.

Tests have also been carried out in accordance with the practices of this invention for converting the hydroxyapatite starting material to a calcium phosphate material which has a higher Ca/P ratio, for example, from the hydroxyapatite Ca/P ratio of 1.66 to a higher Ca/P ratio up to a Ca/P ratio of 2.0. In these tests the starting material was Interpore-200 hydroxyapatite blocks measuring 2.5×2.5×1.2 cm and an Interpore-500 block measuring 2.5×2.5×1.5 cm.

The calcium-contributing or calcium oxide-contributing moiety employed to increase the Ca/P ratio, was an aqueous solution of calcium nitrate. The calcium nitrate was added to the hydroxyapatite blocks by the pipette/wick technique. After the addition of the calcium nitrate solution to the hydroxyapatite blocks, the blocks were placed on a polyethylene plastic mesh in a drying oven at a temperature of 80° F. and 30% relative humidity. The blocks were rotated at approximately 20 minute intervals for 6 hours and left overnight in the oven. Thereupon, the oven was heated to 75° C. and the blocks dried for about 4 hours. The resulting treated, dried blocks were placed on an alumina substrate and placed in a LeMont silicon carbide resistance heated laboratory furnace. The blocks were heated in the presence of air at a temperature of 1350° C. for a period of about 7 hours and then left overnight in the furnace for cooling down.

The blocks were cut in two and microscopic examination showed excellent preservation of the internal pore structure as compared with the hydroxyapatite starting material. X-ray powder diffraction analysis of the firing samples indicated that the treated Interpore-500 material was more completely converted to tetracalcium phosphate Ca$_4$P$_2$O$_9$ than the Interpore-200 material. It was noted that a temperature of below about 1350° C. is not likely usefully satisfactory for the conversion of the hydroxyapatite to tetracalcium phosphate since when the firing is carried out at 1250° C., the conversion takes place too slowly. By firing at a temperature of about 1350° C., the conversion of the hydroxyapatite to tetracalcium phosphate occurs more quickly, about 5-8 hours, more or less.

In these tests the hydroxyapatite material was substantially converted. For example, in one of these tests only about 10% by weight hydroxyapatite remained in the treated hydroxyapatite material, the remainder being at least 50% tetracalcium phosphate. Another test yielded a material which analyzed 50% tetracalcium phosphate, 40% hyroxyapatite. Still another yielded a material which analyzed 60% tetracalcium phosphate and 30% hydroxyapatite. Yet other tests yielded materials which contained primarily, at least about 50-80%, tetracalcium phosphate and a minor, small amount, about 5-10%, of hydroxyapatite.

Further tests were carried out employing granular hydroxyapatite material of the type used in the practices of this invention, particular IP 200 and IP 500 hydroxyapatite. In these tests the granular material measuring 1-2 mm for IP 500 hydroxyapatite 0.425-1.0 mm for IP 200 hydroxyapatite in amounts measuring 41.7 grams for IP 500 and 100.2 grams for IP 200 were separately loaded and mixed in Teflon lined cylinders. With the cylinders tilted about 30° from the horizontal and rotated about their cylindrical axis the mass of the granular material was tumbled therein. For each test there was added 25% by weight of a 1:2 $(NH_4)_2HPO_4:H_2O$, amounting to 8.5% by weight dry ammonium phosphate. The ammonium phosphate solution was slowly added by pipette while the granular material was tumbled.

After the addition of the ammonium phosphate solution tumbling of the wetted granular material was continued intermittently evey 20–30 minutes to prevent too rapid drying of the surface layer granules. The granular material was fired on an alumina substrate, the IP 500 granules were heated at a rate of 400° C. per hour and held at 1125° C. for two hours and ten minutes and the IP 200 granules were heated at a rate of about 600° C. per hour and held at 1125° C. for two hours.

After firing and cooling, the granular materials were analyzed by X-ray powder diffraction and both the IP 500 and the IP 200 granular materials assayed 95% by weight tricalcium phosphate and 5% by weight hydroxapatite, showing the substantially complete conversion of hydroxyapatite, Ca/P ratio of 1.66, to a Ca/P ratio of 1.5, the Ca/P ratio for tricalcium phosphate.

As will be apparent to those skilled in the art in the light of the foregoing disclosure, many modifications, alterations and substitutions are possible in the practice of this invention without departing from the spirit or scope thereof.

What is claimed is:

1. A uniform calcium phosphate-containing material useful as bone substitute material or for the manufacture of prosthetic devices, having a cancellous structure characteristic of boney tissue or bone or a substantially uniformly permeable microporous structure characterized by a substantially uniform pore volume in the range from about 10 to about 90% and by a pronounced three-dimensional fenestrate structure corresponding to the microstructure of the porous carbonate echinoderm or scleractinian coral skeletal material of marine life and providing a periodic minimal surface, said periodic minimal surface dividing the volume of said material into two interpenetrating regions, each of which is a single multiple connected domain, said material having a substantially uniform pore size diameter and substantially uniform pore connections or openings in the range from about 5 microns to about 500 microns, said material comprising a calcium phosphate having a calcium to phosphorus Ca/P atomic ratio in the range 1.0–2.0 and consisting essentially of a mixture of dicalcium phosphate $Ca_2P_2O_7$ and tricalcium phosphate $Ca_3P_2O_8$ or a mixture of tricalcium phosphate $Ca_3P_2O_8$ and hydroxyapatite or a mixture of tetracalcium phosphate $Ca_4P_2O_9$ and hydroxyapatite.

2. A uniform calcium phosphate-containing material in accordance with claim 1 wherein said mixture consists essentially of hydroxapatite and tetracalcium phosphate.

3. A uniform calcium phosphate material in accordance with claim 1 wherein said mixture consists essentially of dicalcium phosphate and tricalcium phosphate.

4. A uniform calcium phosphate material in accordance with claim 2 wherein said mixture contains a major amount of hydroxyapatite.

5. A uniform calcium phosphate-containing material in accordance with claim 2 wherein said mixture comprises a substantially equimolar amount of hydroxyapatite and tetracalcium phosphate.

6. A uniform calcium phosphate material in accordance with claim 2 wherein said- mixture comprises a major molal or a major amount by weight of tetracalcium phosphate.

7. A uniform calcium phosphate material in accordance with claim 3 wherein said mixture comprises a major molal amount or a major amount by weight of dicalcium phosphate.

8. A uniform calcium phosphate material in accordance with claim 3 wherein said mixture comprises a major molal amount or a major amount by weight of tricalcium phosphate.

9. A uniform calcium phosphate material in accordance with claim 1 wherein said mixture consists essentially of dicalcium phosphate.

10. A uniform calcium phosphate material in accordance with claim 1 wherein said mixture consists essentially of tetracalcium phosphate.

11. A uniform calcium phosphate material in accordance with claim 2 wherein said mixture contains about 10–30% by weight of hydroxyapatite and about 90–70% by weight of tetracalcium phosphate.

12. A uniform calcium phosphate material in accordance with claim 11 wherein said mixture Contains 25% by weight hydroxyapatite.

13. A uniform calcium phosphate material in accordance with claim 3 wherein said mixture contains substantially equimolar amounts or substantially equal amounts of dicalcium phosphate and tricalcium phosphate.

14. A uniform calcium phosphate material in accordance with claim 4 wherein said mixture contains about 75% by weight tetracalcium phosphate.

15. A uniform calcium phosphate material in accordance with claim 1 wherein said material comprises substantially only dicalcium phosphate $Ca_2P_2O_7$ and has a calcium to phosphorus Ca/P atomic ratio of about 1.

16. A uniform calcium phosphate material in accordance with claim 1 wherein said material comprises substantially only tricalcium phosphate $Ca_3P_2O_8$ and has a calcium to phosphorus Ca/P atomic ratio of about 1.5.

17. A uniform calcium phosphate material in accordance with claim 1 wherein said material comprises substantially only tetracalcium phosphate $Ca_4P_2O_9$ and has a calcium to phosphorus Ca/P atomic ratio of about 2.0.

18. As an article of manufacture a shaped structure consisting essentially of substantially organic-free uniform calcium phosphate material having a substantially uniformly permeable microporous structure characterized by a substantially uniform pore volume in the range from about 10 to about 90% and by a pronounced three-dimensional fenestrate structure corresponding to the microstructure of the porous carbonate echinoderm or scleractinian coral skeletal material of marine life and providing a periodic minimal surface, said periodic minimal surface dividing the volume of said material comprising said shaped structure into two interpenetrating regions, each of which is a single multiple connected domain, said material having a substantially uniform pore size diameter and substantially uniform pore connections or openings int eh range from about 5 microns to about 500 microns, said material comprising a calcium phosphate having a calcium to phosphorus Ca/P atomic ratio in the range 1.0–2.0 and consisting $Ca_2P_2O_7$ and tricalcium phosphate $Ca_3P_2O_8$ or a mixture of tricalcium phosphate $Ca_3P_2O_8$ and hydroxyapatite or a mixture of tetracalcium phosphate $Ca_4P_2O_9$ and hydroxyapatite.

19. A shaped structure in accordance with claim 18 wherein said mixture consists essentially of tricalcium phosphate and hydroxyapatite.

20. A shaped structure in accordance with claim 18 wherein said mixture consists essentially of tetracalcium phosphate and hydroxyapatite.

21. A shaped structure in accordance with claim 18 wherein said mixture consists essentially of dicalcium phosphate and tricalcium phosphate.

22. Finely divided substantially organic-free uniform calcium phosphate material useful as bone substitute material and the like, the particles making up said finely divided calcium phosphate material having a substantially uniformly permeable microporous structure characterized by a substantially uniform pore volume in the range of from about 10 to about 90% by a pronounced three-dimensional fenestrate structure corresponding to the microstructure of the porous carbonate echinoderm or scleractinian coral skeletal material of marine life and providing a periodic minimal surface, said periodic minimal surface dividing the volume of said material into two interpenetrating regions, each of which is a single multiple connected domain, said material having a substantially uniform pore size diameter and substantially uniform pore connections or openings in the range from about 5 microns to about 500 microns, said material comprising a calcium phosphate having a calcium phosphorus Ca/P atomic ratio in the range 1.0–2.0, and consisting essentially of a mixture of dicalcium phosphate $Ca_2P_2O_7$ and tricalcium phosphate $Ca_3P_2O_8$ or a mixture of tricalcium phosphate $Ca_3P_2O_8$ and hydroxyapatite or a mixture of hydroxyapatite and tetracalcium phosphate $Ca_4P_2O_9$.

23. Finely divided calcium phosphate material in accordance with claim 22 wherein said material consists essentially of tricalcium phosphate and hydroxyapatite.

24. Finely divided calcium phosphate material in accordance with claim 22 wherein said material consists essentially of dicalcium phosphate, tricalcium phosphate and also contains hydroxyapatite.

25. Finely divided organic-free calcium phosphate material in accordance with claim 22 wherein said finely divided calcium phosphate material comprises substantially only dicalcium phosphate $Ca_2P_2O_7$ and has a calcium to phosphorus Ca/P atomic ratio of about 1.0.

26. Finely divided substantially organic-free calcium phosphate material in accordance with claim 16 wherein said substantially organic-free calcium phosphate material comprises substantially only tricalcium phosphate $Ca_3P_2O_8$ and has a calcium to phosphorus Ca/P atomic ratio of about 1.5.

27. Finely divided substantially organic-free calcium phosphate material in accordance with claim 22 wherein said organic-free calcium phosphate material comprises substantially only tetracalcium phosphate $Ca_4P_2O_9$ and has a calcium to phosphorus Ca/P atomic ratio of about 2.0.

28. A method of converting calcium hydroxyapatite material having a calcium to phosphorus Ca/P atomic ratio of 1.66 to a uniform calcium phosphate material useful as bone substitute material or for the manufacture of prosthetic devices, said hydroxyapatite material having a substantially uniformly permeable microporous structure characterized by a substantially uniform pore volume in the range from about 10 to about 90% and by a pronounced three-dimensional fenestrate structure corresponding to the microstructure of the porous carbonate echinoderm or scleractinian coral skeletal material of marine life and providing a periodic minimal surface, said periodic minimal surface dividing the volume of said hydroxyapatite material into two interpenetrating regions, each of which is a single multiple connected domain, said hydroxyapatite material having a substantially uniform pore size diameter and substantially uniform pore connections or openings in the range from about 5 microns to about 500 microns, said calcium phosphate material having a calcium to phosphorus Ca/P atomic ratio lower than 1.66 and consisting essentially of a mixture of dicalcium phosphate $Ca_2P_2O_7$ and tricalcium phosphate $Ca_3P_2O_8$ which comprises contacting said hydroxyapatite material with a phosphate solution to effect substantially uniform wetting of said hydroxyapatite material by said phosphate solution, drying the resulting treated hydroxyapatite material to effect deposition of the phosphate from said solution substantially uniformly onto the surface of said hydroxyapatite material and heating or firing the resulting phosphate treated hydroxyapatite material to decrease the calcium to phosphorus Ca/P atomic ratio thereof to a value less than 1.66 to produce a calcium phosphate material consisting essentially of a mixture of dicalcium phosphate $Ca_2P_2O_7$ and tricalcium $Ca_3P_2O_8$ or a mixture of dicalcium phosphate $Ca_2P_2O_7$ tricalcium phosphate $Ca_3F_2O_8$ and hydroxyapatite.

29. A method in accordance with claim 28 wherein said phosphate solution contains a phosphoric acid.

30. A method in accordance with claim 28 wherein said phosphate solution is aqueous phosphoric acid $H_3PO_4$.

31. A method in accordance with claim 28 wherein said phosphate solution contains ammonium phosphate.

32. A method in accordance with claim 31 wherein said ammonium phosphate is diammonium phosphate.

33. A method in accordance with claim 28 wherein said hydroxyapatite material is heated or fired to a temperature in the range about 1000°–1250° C.

34. A method in accordance with claim 28 wherein said hydroxyapatite material is heated or fired to a temperature in the range about 1150°–1175° C.

35. A method of converting calcium hydroxyapatite material having a calcium to phosphorus Ca/P atomic ratio of 1.66 to a uniform phosphate material useful as bone substitute material or for the manufacture of prosthetic devices, said hydroxyapatite material having a substantially uniformly permeable microporous structure characterized by a substantially uniform pore volume in the range from about 10 to about 90% and by a pronounced three-dimensional fenestrate structure corresponding to the microstructure of the porous carbonate echinoderm or scleractinian coral skeletal material of marine life and providing a periodic minimal surface, said periodic minimal surface dividing the volume of said hydroxyapatite material into two interpenetrating regions, each of which is a single multiple connected domain, said hydroxyapatite material having a substantially uniform pore size diameter and substantially uniform pore connections or openings in the range from about 5 microns to about 500 microns, said calcium phosphate material having a calcium to phosphorus Ca/P atomic ratio greater than 1.66 and up to 2.0 and containing tetracalcium phosphate $Ca_4P_2O_9$ which comprises contacting said hydroxyapatite material with a calcium-containing solution to effect substantially uniform absorption or wetting of said calcium-containing solution by said hydroxyapatite material or substantially uniform wetting of said hydroxyapatite material by said calcium-containing solution, drying the resulting treated hydroxyapatite material to effect deposition of the calcium-containing component of said solution substantially uniformly onto the surface of said hydroxyapatite material and heating or firing the resulting calcium treated hydroxyapatite material to increase the Calcium to phosphorus Ca/P atomic ratio thereof to a value greater than 1.66 and up to 2.0 and to produce a calcium phosphate material consisting essentially of a mixture of hydroxyapatite and tetracalcium phosphate $Ca_4P_2O_9$.

36. A method in accordance with claim 35 wherein said calcium-containing solution is an aqueous solution of a calcium-containing compound.

37. A method in accordance with claim 35 wherein said calcium-containing solution is an aqueous solution of calcium nitrate.

38. A method in accordance with claim 35 wherein said calcium-containing solution is a solution containing calcium hydroxide.

39. A method in accordance with claim 35 wherein said calcium-containing solution is an aqueous solution containing a calcium compound selected from the group consisting of calcium nitrate, calcium acetate, calcium chloride, calcium perchorate, calcium hypochlorite, calcium propionate and calcium butyrate.

40. A method in accordance with claim 35 wherein said hydroxyapatite material is heated or fired to a temperature in the range about 1300°–1400° C.

41. A method in accordance with claim 35 wherein said hydroxyapatite material is heated or fired to a temperature in the range about 1250°–1350° C.

42. A method of converting calcium hydroxyapatite material having a calcium to phosphorus Ca/P atomic ratio of 1.66 to a uniform calcium phosphate material useful as bone substitute material or of the manufacture of prosthetic devices, said hydroxyapatite material having a substantially uniformly permeable microporous structure characterized by a substantially uniform pore volume in the rang e from about 10 to about 90% and by a pronounced three-dimensional fenestrate structure corresponding to the microstructure of the porous carbonate echinoderm or scleractinian coral skeletal material of marine life and providing a periodic minimal surface, said periodic minimal surface dividing the volume of said hydroxyapatite material into two interpenetrating regions, each of which is a single multiple connected domain, said hydroxyapatite material having a substantially uniform pore size diameter and substantially uniform pore connections or openings in the range from about 5 microns to about 500 microns, said calcium phosphate material having a calcium to phosphorus Ca/P atomic ratio lower than 1.66 and consisting essentially of a mixture of dicalcium phosphate $Ca_2P_2O_7$ and tricalcium phosphate $Ca_3P_2O_8$ or a mixture of tricalcium phosphate and hydroxapatite or said calcium phosphate material having a calcium to phosphorus Ca/P atomic ratio greater than 1.66 and containing hydroxyapatite and tetracalcium phosphate $Ca_4P_2O_9$ which comprises contacting said hydroxyapatite material with a phosphate solution or with a calcium-containing solution to effect substantially uniform absorption of said phosphate solution or said calcium-containing solution by said hydroxyapatite material or substantially uniform wetting of said hydroxyapatite material by said phosphate solution or said calcium-containing solution, drying the resulting treated hydroxyapatite material to effect deposition of the phosphate from said phosphate solution or the calcium from said calcium-containing solution onto the surface of said hydroxyapatite material and heating or firing the resulting treated hydroxapatite material to decrease the calcium to phosphorus Ca/P atomic ratio thereof to a value less than 1.66 and in the range 1.0–1.5 and to produce a calcium phosphate material consisting essentially of a mixture of dicalcium phosphate $Ca_2P_2O_7$ and tricalcium phosphate $Ca_3P_2O_8$ when the solution applied to said hydroxyapatite material is said phosphate solution and to produce a calcium phosphate material having a calcium to phosphate Ca/P atomic ratio greater than 1.66 and up to 2.0 and consisting essentially of hydroxyapatite and tetracalcium phosphate $Ca_4P_2O_9$ when said solution is a calcium-containing solution.

43. A method of treating calcium phosphate material, said calcium phosphate material having a substantially uniform permeable microporous structure characterized by a substantially uniform pore volume in the rang from about 10 to about 90% and by a pronounced three-dimensional fenestrate structure corresponding to the microstructure of the porous echinoderm or scleractinian coral skeletal material of marine life and providing a periodic minimal surface, said periodic minimal surface dividing the volume of said calcium phosphate material into two interpenetrating regions, each of which is a single multiple-connected domain, said calcium phosphate material having a substantially uniform pore size diameter and substantially uniform pore connections or openings in the range from about 5 microns to about 500 microns, said calcium phosphate material having a calcium to phosphorus Ca/P atomic ratio in the range 1.0 to 2.0 to change the Ca/P ratio to a higher value in the range 1.0–2.0 which comprises, wherein the Ca/P ratio of said calcium phosphate material is 1.0 or greater but less than 2, adding or incorporating a solution of a calcium-contributing moiety to said calcium phosphate material and firing the resulting treated calcium phosphate material to yield a fired uniform calcium phosphate produce which has a calcium to phosphate atomic ratio greater than the Ca/P ratio of said calcium phosphate material.

44. A method of treating a calcium phosphate material wherein said calcium phosphate material has a substantially uniformly permeable microporous structure characterized by a substantially uniform pore volume in the range from about 10 to about 90$ and by a pronounced three-dimensional fenestrate structure corresponding to the microstructure of the porous echinoderm or sceleratinian coral skeletal material of marine life and providing a periodic minimal surface, said periodic minimal surface dividing the volume of said calcium phosphate material into tow interpenetrating regions, each of which is a single multiple-connected domain, said calcium phosphate material having a substantially uniform pore size diameter and substantially uniform pore connections or openings in the range from about 5 microns to about 500 microns, said calcium phosphate material having calcium to phosphate Ca/P atomic ratio in the range 1.0 to 2.0 to change the Ca/P ratio to a lower value in the range 1.0–2.0, which comprises, where the Ca/P ratio of said calcium phosphate material is 2.0 or less but greater than 1, adding or incorporating a phosphate-contributing or phosphorus-contributing moiety to said calcium phosphate material and firing the resulting treated calcium phosphate material to yield a fired uniform calcium phosphorus product which has a calcium to phosphate atomic ratio less than the Ca/P ratio of said calcium phosphate material.

* * * * *